(12) United States Patent
Nampalli et al.

(10) Patent No.: US 7,446,227 B2
(45) Date of Patent: Nov. 4, 2008

(54) PROCESS FOR PREPARATION OF 5H-DIBENZO[A,D] CYCLOHEPTENE DERIVATIVES

(75) Inventors: Satyam Nampalli, Belle Mead, NJ (US); Brijesh Patel, Piscataway, NJ (US); Peter Xavier Tharial, Piscataway, NJ (US); Ravishanker Kovi, Monroe, NJ (US)

(73) Assignee: Apicore, LLC, Somerset, NJ (US)

( * ) Notice: Subject to any disclaimer, the term of this patent is extended or adjusted under 35 U.S.C. 154(b) by 0 days.

(21) Appl. No.: 11/609,075

(22) Filed: Dec. 11, 2006

(65) Prior Publication Data

US 2008/0139848 A1    Jun. 12, 2008

(51) Int. Cl.
    *C07C 211/00*    (2006.01)
(52) U.S. Cl. ..................................... 564/337
(58) Field of Classification Search ............. None
    See application file for complete search history.

(56) References Cited

U.S. PATENT DOCUMENTS 3,332,977 A * 7/1967 Wendler .................. 558/44
5,616,716 A   4/1997 Dull et al.
5,932,767 A   8/1999 Hoerrner et al.

FOREIGN PATENT DOCUMENTS

GB       11034486      *  6/1966

OTHER PUBLICATIONS

Caporusso et al, Stereoselective Synthesis of Chiral 3-Aryl-1-alkynes from Bromoalienes and heterocuprates, 2006, Published on Web (Sep. 2, 2006), J. Org. Chem., vol. 71, pp. 1902-1910, especially p 1907, para. D.

* cited by examiner

*Primary Examiner*—Samuel A Barts
(74) *Attorney, Agent, or Firm*—Timothy X. Gibson; Kaplan Gilman Gibson & Dernier LLP

(57) ABSTRACT

A process for preparation of protriptyline hydrochloride from 5-dihydrobenzocycloheptatriene of formula (1) by coupling with chloropropyl alcohol in the presence of excess n-butyl Lithium in tetrahydrofuran under inert atmosphere, followed by preparation of mesylate derivative of formula (3) and finally the nucleophilic displacement of the mesylate group by reacting methylamine solution in methanol to give protriptyline free base of the formula (4). Also the present process reveals the hydrochloride salt formation and purification of the same to give pure pharmaceutical grade protriptyline hydrochloride with impurities less than 0.1% w/w.

7 Claims, No Drawings

PROCESS FOR PREPARATION OF 5H-DIBENZO[A,D] CYCLOHEPTENE DERIVATIVES

BACKGROUND OF THE INVENTION

The present invention relates to processes for preparing dibenzocycloheptene compounds and specifically to novel processes for the production of 5H-dibenzo[a,d] cycloheptene derivatives which are substituted at 5-position, more particularly N-methyl-5H-dibenzo (a,d)-cycloheptene-5-propanamine hydrochloride.

Protriptyline hydrochloride is a dibenzocycloheptatriene derivative with the chemical name N-methyl-5H-dibenzo (a,d)-cycloheptene-5-propanamine hydrochloride. Protriptyline hydrochloride is used as an antidepressant under the trade name VIVACTIL™ and is supplied as tablets in strengths of 5 and 10 mg.

U.S. Pat. No. 5,932,767 assigned to Merck & Co., Inc. discloses the preparation of protriptyline from 5-dihydrodibenzocycloheptatriene, by deprotonation, followed by reaction at low temperatures with 1,3-bromochloropropane to give the 5-(chloropropyl)-dibenzocycloheptatriene, which is reacted with methylamine in a displacement reaction to give the protriptyline product.

SUMMARY OF THE INVENTION

An object of the present invention is to provide a simple, cost-effective and reliable process for the preparation of protriptyline hydrochloride.

Another object of the invention is to provide a simple, cost-effective and reliable process for preparation of the intermediate 3-(5H-Dibenzo[a,d]cyclohepten-5-yl)-propan-1-ol of the formula (2).

Still another object of the invention is to provide a simplified procedure for the isolation of 3-(5H-Dibenzo[a,d]cyclohepten-5-yl)-propan-1-ol of the formula (2) hereinbelow which is desired for generating a compound having formula (3) hereinbelow having a suitable leaving group such as mesylate, tosylate, besylate or acetyl. In one embodiment this achieved using methane sulfonyl chloride.

Yet another object of the invention is to provide a process whereby the compound of formula (3) which upon reaction with methyl amine gives rise to the compound 5-(N-methyl-aminopropyl) dibenzocycloheptatriene of formula (4). These and other aspects of the invention will be apparent to those skilled in the art.

DETAILED DESCRIPTION OF THE PREFERRED EMBODIMENTS

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

In accordance with one embodiment the present invention relates to novel processes for the production of 5H-dibenzo [a,d] cycloheptene derivatives which are substituted at the 5-position. In one embodiment, N-methyl-5H-dibenzo (a,d)-cycloheptene-5-propanamine hydrochloride is prepared by reacting 5-dihydro dibenzocycloheptatriene with chloro propyl alcohol in the presence of an excess of n-butyl lithium solution. The resulting product is converted to a mesylate, tosylate, besylate or acetyl derivative, followed with a nucleophilic displacement reaction using methylamine in methanol, water or tetrahydrofuran. The resulting product is then converted to protryptylene hydrochloride.

Scheme

The following provides a process for the production of protriptyline hydrochloride of formula (5):

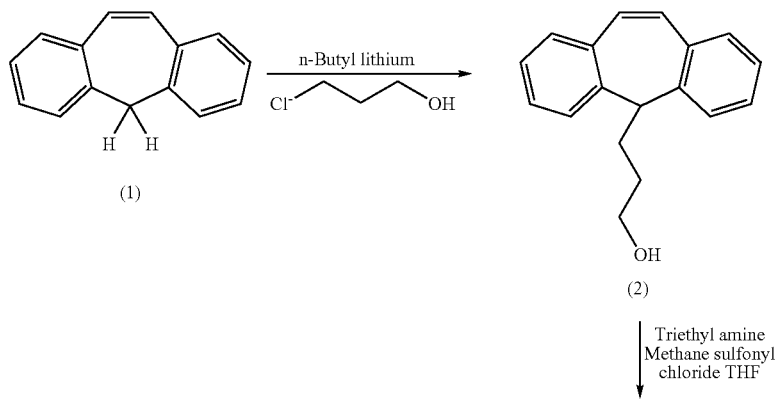

-continued

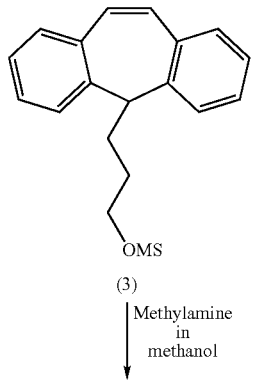

(3)

Methylamine in methanol

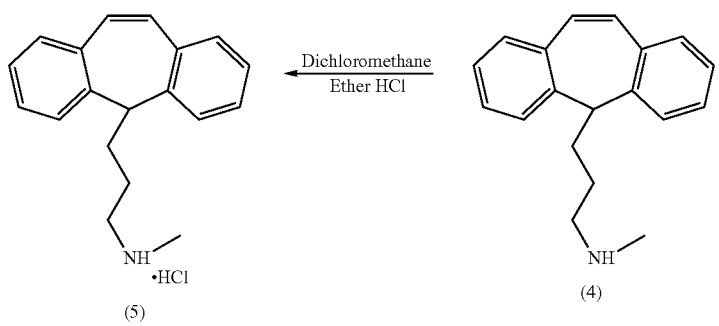

Experimental Procedures

Thus, in accordance with an embodiment the present invention a first step involves condensation of the starting material of the formula (1) to 3-(5H-Dibenzo[a,d]cyclohepten-5-yl)-propan-1-ol of the formula (2).

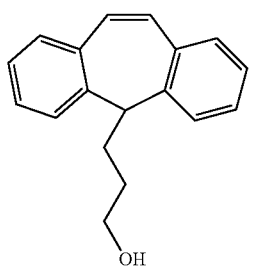

(2)

In one example the process for this transformation involves inert reaction between excess equivalent of n-butyl lithium and chloropropyl alcohol with starting material of formula (1) at −15° C. to −20° C. in dry tetrahydrofuran. After 4.0 hours reaction, reaction mass was quenched with water. Upon distillation of organic layer gives crude 3-(5H-Dibenzo[a,d]cyclohepten-5-yl)-propan-1-ol of the formula (2). Crude product upon high vacuum distillation gives pure 3-(5H-Dibenzo[a,d]cyclohepten-5-yl)-propan-1-ol of the formula (2) in 65-75% yield range.

The second step of this process involves formation of formula (3) from 3-(5H-Dibenzo[a,d]cyclohepten-5-yl)-propan-1-ol of the formula (2).

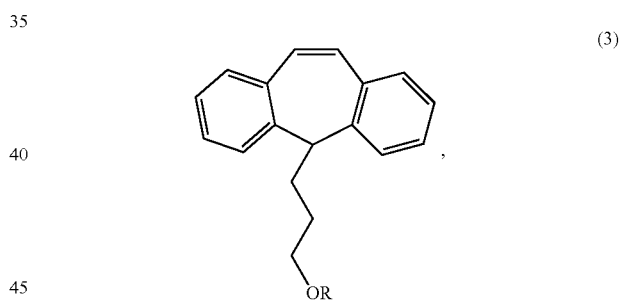

(3)

wherein R denotes a mesylate, tosylate, besylate or acetyl group.

In one example this reaction was carried out in inert conditions. 3-(5H-Dibenzo[a,d]cyclohepten-5-yl)-propan-1-ol of the formula (2) was dissolved in dry tetryhydrofuran and cooled down to 0° C.-5° C. Triethyl amine (1.5 eq.) was added followed by methane sulfonyl chloride (1.2 eq.) drop wise at 0° C.-5° C. After addition, the reaction mass temperature was raised to room temperature. The reaction mass was quenched with water and the organic layer was washed with brine solution. The solvent was distilled out under reduced pressure which yielded a light yellow color viscous compound, namely, the mesylate derivative of formula (3) in 90-95% yield.

The third step of the invention involves nucleophilic displacement of the mesylate group in formula (3) with methylamine solution in methanol which gives rise to the compound 5-(N-methyl-aminopropyl) dibenzocycloheptatriene of formula (4).

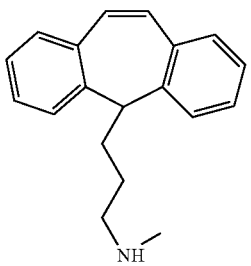

(4)

In one example of this step the mesylate derivative of formula (3) and methylamine solution were mixed in methanol and refluxed for 2.0 hours. After 2.0 hours the solvent was distilled out under reduced pressure. The remaining residue was dissolved in water and pH was adjusted to 2.0 to 3.0 with concentrated HCL. One isopropyl ether washing was given to the aqueous solution. The pH was adjusted to 6.0 and given one isopropyl ether washing. pH was adjusted to 7.0 and given one more IPE wash. The aqueous layer was basified with ammonium hydroxide and extracted with dichloromethane. The organic layer was washed with water followed by brine solution and dried using sodium sulfate in the solution. The solution was filtered with sodium sulfate and washed with dichloromethane. To the filtrate charcoal was added and stirred for 1 hour at 25-30° C. The reaction mass was filtered through a celite bed and washed with dichloromethane.

The fourth step of the present process invention involves conversion of the 5-(N-methyl-aminopropyl) dibenzocycloheptatriene (4) to protriptyline hydrochloride (5) using ether HCl and dichloromethane.

In one example this step was carried out by distilling the dichloromethane from the 5-(N-methyl-aminopropyl) dibenzocycloheptatriene formula (4) residue under reduced pressure. Fresh dichloromethane was added to dissolve the residue. The solution was cooled to 5° C. to 10° C. After addition, dichloromethane was distilled out under vacuum. The residue was co-distilled twice with ethyl acetate. To the residue was added ethyl acetate and the reaction mass cooled to room temperature. The reaction mass was stirred for 5-6 hours at room temperature. The solid formed was filtered and washed with ethyl acetate and vacuum dried.

Purification of crude protriptyline hydrochloride was carried out by making a slurry by taking the above wet cake in 4 volumes of toluene and heated to 80° C. with stirring. At the same temperature the slurry was stirred for a half-hour. The reaction mass was cooled to room temperature and the solid filtered and washed with acetone. The wet cake was subjected to two acetone hot leachings. This yielded a pure protriptyline hydrochloride with chemical name N-methyl-5H-dibenzo (a,d)-cycloheptene-5-propanamine hydrochloride of formula (5) in 20-30% yield range to afford 99.95% to 100.00% pure material by HPLC.

Examples 3-(5H-Dibenzo[a,d]cyclohepten-5-yl)-propan-1-ol of the Formula (2)

200 gm of starting material of formula (1) was charged into a 10 L three-neck flask containing dried tetrahydrofuran, under nitrogen atmosphere. The reaction mass was cooled to −15° C. to −20° C. n-butyl lithium solution 4.0 eq. (1.6 M in hexane) was added drop wise. After addition, the reaction mass was stirred for 2.0 hours at −10° C. to −15° C. To the reaction mass was added 3-chloropropyl alcohol 1.05 eq. drop wise at −15 to −20° C. After addition, the reaction mass was stirred for 2.0 hours at −10° C. to −15° C. Completion of the reaction was checked by TLC. The reaction mass was quenched with water. The organic layer was washed with brine solution and dried with sodium sulfate. Solvent was removed under reduced pressure to afford crude light yellow color viscous liquid product 3-(5H-Dibenzo[a,d]cyclohepten-5-yl)-propan-1-ol of the formula (2) in 300.0 gm yield.

Purification of Crude 3-(5H-Dibenzo[a,d]cyclohepten-5-yl)-propan-1-ol of the Formula (2)

The crude product 3-(5H-Dibenzo[a,d]cyclohepten-5-yl)-propan-1-ol of the formula (2) was subjected to high vacuum fractional distillation. The first fraction was collected at vapor temperature 48° C.-55° C. The second fraction was collected at vapor temperature 120° C.-165° C. The product fraction was collected at vapor temperature 165° C.-195° C. to afford light green color to colorless product of 3-(5H-Dibenzo[a,d]cyclohepten-5-yl)-propan-1-ol of the formula (2) in 135-145 gm (50%) yield.

Mesylate Derivative of Formula (3)

3-(5H-Dibenzo[a,d]cyclohepten-5-yl)-propan-1-ol of the formula (2) (100.0 gm) was charged into a 2.0 L single neck flask and dissolved in dried tetrahydrofuran under nitrogen atmosphere and Cooled to 0° C.-5° C. Triethyl amine (84.5 mL, 1.5 eq.) was added drop wise at 0° C.-5° C. followed by drop wise addition of methane sulfonyl chloride (37.3 mL, 1.2 eq.) at 0° C. 5° C. The reaction mass temperature was raised to room temperature. Completion of the reaction was checked by TLC. The reaction mass was quenched with water and a brine wash was given. The organic layer was dried over sodium sulfate. Solvent was removed under reduced pressure to afford light yellow color viscous product mesylate derivative compound of formula (3) (130 to 135 gm).

5-(N-methyl-aminopropyl) dibenzocycloheptatriene of Formula (4)

The mesylate derivative of formula (3) 100.0 gm was charged into a 2.0 L single neck flask. 582 ml (20 eq) of methylamine solution in methanol (30%) was added into the flask. The reaction mass was heated to reflux temperature (65'-70° C.) and stirred at reflux temperature for 2.0 hours. Completion of the reaction was checked by TLC. The solvent was removed under reduced pressure. The residue was dissolved in water at pH 3.0 and given an isopropyl ether wash. The isopropyl ether wash was repeated at pH 6.0 and again at pH 7.0. The aqueous layer was basified and extracted with dichloromethane. The organic layer was washed with water, followed by brine solution and dried over sodium sulfate to obtain 5-(N-methyl-aminopropyl) dibenzocycloheptatriene of formula (4).

Protriptyline Hydrochloride of Formula (5)

Charcoal (15 gm) was added to 5-(N-methyl-aminopropyl) dibenzocycloheptatriene of formula (4) and stirred for 1.0 hour at 25° C. to 30° C. The contents of the flask were filtered through a celite bed and washed with dichloromethane. The dichloromethane solution was distilled atmospherically 40° C. to 45° C. up to half of the volume. The reaction mass was cooled to 20° C.-25° C. and chilled to 5° C. to 10° C. 37.0 mL of ether HCl (15-20%) was added drop wise into the reaction mass at 5° C. to 110° C. After this addition the dichloromethane was distilled out completely under vacuum. To the reaction mass ethyl acetate (300 mL) was added and the reaction mass was cooled to 25° C. to 30° C. The reaction mass was further stirred for 5-6 hours at 25° C. to 30° C. The resulting solid was filtered and washed with ethyl acetate and vacuum dried yielding 40 gm of wet cake crude protriptyline hydrochloride of formula (5).

Purification of Protriptyline Hydrochloride (5)

Crude protriptyline hydrochloride (5) 40.0 gm was charged into a 500 ml single neck flask. 160 mL of toluene was added. The slurry was heated to 80° C. to 85° C. and stirred for 60 minutes. The reaction mass was cooled to room temperature and the solid was filtered off and washed with acetone. The product was dried at 70° C. under vacuum for 15-20 hours to afford white color solid (40.0 gm).

40.0 gm of the above dried product was charged into a 500 ml single neck flask. 200 mL of acetone was added and the slurry was heated to reflux temperature and stirred for 60 minutes. The reaction mass was cooled to room temperature and the solid was filtered off and washed with acetone. The product was suck dried well to afford white color wet cake (35.0 gm).

35.0 gm of the above prepared wet cake was charged into a 500 ml single neck flask. 200 mL of acetone was added and the slurry was heated to reflux temperature and stirred for 60 minutes. The reaction mass was cooled to room temperature and the solid was filtered off and washed with acetone. The product was suck dried well to afford white color wet cake (30.0 gm). The resulting wet cake was dried at 60° C. under vacuum for 20 hours. After drying the 22.0 gm of dried protriptyline hydrochloride was unloaded. The dried protryptilene was substantially pure, having a purity of greater than 99.9%.

While the preferred embodiments have been described and illustrated it will be understood that changes in details and obvious undisclosed variations might be made without departing from the spirit and principle of the invention and therefore the scope of the invention is not to be construed as limited to the preferred embodiment.

What is claimed is:

1. A process of preparing N-methyl-5H-dibenzo (a,d)-cycloheptene-5-propanamine hydrochloride comprising reacting 5-dihydro dibenzocycloheptatriene with chloro propyl alcohol in the presence of an excess of n-butyl lithium to obtain 3-(5H-Dibenzo[a,d]cyclohepten-5-yl)-propan-1-ol, converting the resulting product to a compound having the formula

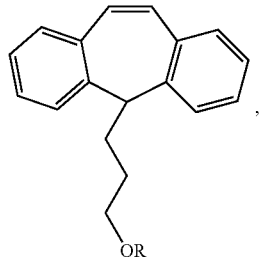

(3)

wherein R is a leaving group, reacting the compound of formula (3) with methylamine solution in methanol to produce 5-(N-methyl-aminopropyl) dibenzocycloheptatriene and converting 5-(N-methyl-aminopropyl) dibenzocycloheptatriene to N-methyl-5H-dibenzo (a,d)-cycloheptene-5-propanamine hydrochloride.

2. The process according to claim 1 wherein R denotes a mesylate, a tosylate, a besylate or an acetyl group.

3. The process according to claim 1, the conversion of 5-(N-methyl-aminopropyl) dibenzocycloheptatriene to N-methyl-5H-dibenzo (a,d)-cycloheptene-5-propanamine hydrochloride comprising dissolving 5-(N-methyl-aminopropyl) dibenzocycloheptatriene in isopropyl ether, and adding to the solution HCl solution in ether.

4. A process of purifying N-methyl-5H-dibenzo (a,d)-cycloheptene-5-propanamine hydrochloride prepared according to claim 1 comprising leaching the compound with toluene and a compound selected from the group consisting of hot acetone, acetonitrile and ethyl acetate.

5. The process of claim 1 wherein the step of preparing 3-(5H-Dibenzo[a,d]cyclohepten-5-yl)-propan-1-ol comprises using 4 eq. of n-butyllithium and 1.05 eq. of 3-chloropropyl alcohol.

6. The process according to claim 1 wherein the step of preparing the compound of formula (3) comprises using 1.5 eq. of an organic base and 1.2 eq. of a compound selected from the group consisting of methane sulfonyl chloride, toluene sulfonyl chloride and benzene sulfonyl chloride in tetrahydrofuran.

7. The process according to claim 6 wherein said organic base is triethyl amine.

* * * * *